US009801924B2

(12) United States Patent
Wolgen

(10) Patent No.: US 9,801,924 B2
(45) Date of Patent: Oct. 31, 2017

(54) THERAPY FOR VITILIGO

(71) Applicant: Clinuvel Pharmaceuticals Limited, Melbourne, VIC (AU)

(72) Inventor: Philippe Wolgen, Melbourne (AU)

(73) Assignee: Clinuvel Pharmaceuticals Limited, Melbourne (AU)

( * ) Notice: Subject to any disclaimer, the term of this patent is extended or adjusted under 35 U.S.C. 154(b) by 707 days.

(21) Appl. No.: 13/801,816

(22) Filed: Mar. 13, 2013

(65) Prior Publication Data

US 2013/0203670 A1  Aug. 8, 2013

Related U.S. Application Data

(63) Continuation-in-part of application No. 12/934,024, filed as application No. PCT/EP2009/000265 on Mar. 27, 2009.

(30) Foreign Application Priority Data

Mar. 27, 2008 (AU) ............................... 2008901461

(51) Int. Cl.
*A61K 38/34* (2006.01)
*A61K 38/22* (2006.01)
*A61K 45/06* (2006.01)
*A61N 5/06* (2006.01)

(52) U.S. Cl.
CPC ............. *A61K 38/22* (2013.01); *A61K 38/34* (2013.01); *A61K 45/06* (2013.01); *A61N 5/062* (2013.01); *A61N 5/0616* (2013.01); *A61N 2005/0661* (2013.01)

(58) Field of Classification Search
CPC .................................................... A61K 38/34
USPC ....................................................... 514/10.7
See application file for complete search history.

(56) References Cited

U.S. PATENT DOCUMENTS

| 4,457,864 A | 7/1984 | Hruby et al. |
| 4,485,039 A | 11/1984 | Hruby et al. |
| 4,866,038 A | 9/1989 | Hruby et al. |
| 4,918,055 A | 4/1990 | Hruby et al. |
| 5,049,547 A | 9/1991 | Hruby et al. |
| 5,674,839 A | 10/1997 | Hruby et al. |
| 5,714,576 A | 2/1998 | Hruby et al. |
| 5,990,091 A | 11/1999 | Tartaglia et al. |
| 2005/0142078 A1 | 6/2005 | Dorr et al. |
| 2006/0029637 A1 | 2/2006 | Tice et al. |
| 2010/0104521 A1 | 4/2010 | Dal Farra et al. |
| 2010/0152119 A1 | 6/2010 | Dal Farra et al. |
| 2011/0130705 A1 | 6/2011 | Wolgen |

FOREIGN PATENT DOCUMENTS

| AU | 597630 | 8/1987 |
| AU | 618733 | 11/1988 |
| WO | 87/04623 | 8/1987 |
| WO | 91/19481 | 12/1991 |
| WO | 98/00166 | 1/1998 |
| WO | 99/60164 | 11/1999 |
| WO | 2006/012667 | 2/2006 |
| WO | 2006/037188 | 4/2006 |
| WO | 2008/025094 | 3/2008 |

OTHER PUBLICATIONS

Anbar T. S. (Photodermatology, Photoimmunology & Photomedicine, 22(3), 157-163, 2006).*
Kanwar (International Journal of Dermatology 44(1), 57-60, 2005).*
Nicolaidou E., (Journal of the American Academy of Dermatology, (Feb. 2007) vol. 56, No. 2, pp. 274-278.*
Njoo M D (Journal of the American Academy of Dermatology 42(2), Part 1, pp. 245-253, 2000).*
Lotti T M (Journal of the European Academy of Dermatology and Venereology: JEADV 13(2), 102-108 (1999).*
Scherschun L (Journal of the American Academy of Dermatology 44(6), 999-1003, 2001).*
Tobin D J (The Journal of pathology 191(4), 407-416, 2000).*
Kanwar et al., Int. J. Dermatol., "Narrow-band UVB for the treatment of vitiligo: an emerging effective and well-tolerated therapy," 44: 57-60 (2005).
"Philips lamps for Phototherapy treatment," Philips Phototherapy range brochure (2012).
"Light sources for phototherapy," Philips Phototherapy treatment brochure (2009).
"Clinuvel Pharmaceuticals' U.S. trial shows positive results of accelerated repigmentation in people," Proactive Investors (2011).
"Q&A: SCENESSE® successful in Phase IIa vitiligo study," Clinuvel announcement (2013).
"Afamelanotide and Narrow-Band Ultraviolet B (NB-UVB) Light in the Treatment of Nonsegmental Vitiligo (NSV)," Clinical trials database (2013).
"Afamelanotide and Narrow-Band Ultraviolet B (NB-UVB) Light in the Treatment of Nonsegmental Vitiligo (NSV) (CUV102)," Clinical trials database (2013).
Re-pigmentation therapy in vitiligo; affects more than 45 million individuals [online]. Clinuvel, 2013 [retrieved on Jan. 18, 2013]. Retrieved from the Internet: <URL: http://www.clinuvel.com/en/scenesse/clinuvels-program-%E2%80%93-nonsegmental-vitiligo>.
EADV MSH society subspecialty meeting programme (2011).
"SCENESSE® successful in Phase IIa vitiligo study," Clinuvel announcement (2012).
Clinical Study Results—US Phase IIa Vitiligo Study CUV102, Clinuvel (2012).
"SCENESSE® European pre-marketing phase," Clinuvel update (2013).
"SCENESSE® data to be presented at American Academy of Dermatology, San Gallicano Rare Disease conferences," Clinuvel announcement (2013).
"Clinuvel Communiqué," Clinuvel newsletter (2012).

(Continued)

*Primary Examiner* — David Lukton

(74) *Attorney, Agent, or Firm* — Lisa V. Mueller; Michael Best & Friedrich LLP

(57) ABSTRACT

The present invention relates to a therapy for vitiligo. In particular the present invention provides a pharmaceutical composition comprising an alpha melanocyte stimulating hormone (alpha-MSH) analog either alone, in combination with narrow band UVB and/or in combination with one or more corticosteroids, immunosuppressants, anti-inflammatory agents and/or photochemotherapeutic agents for the treatment or prevention of vitiligo.

9 Claims, No Drawings

(56) References Cited

OTHER PUBLICATIONS

"Observations from Clinuvel's vitiligo and EPP programs being presented at the American Academy of Dermatology," Clinuvel announcement (2012).
"Safety and Efficacy of Afamelanotide Implants and NB-UVB versus NB-UVB Alone in the Treatment of Nonsegmental Vitiligo," American Academy of Dermatology preliminary results presentation (2012).
"Melanogenesis and Photoprotection," Clinuvel Pharmaceuticals Annual General Meeting presentation (2012).
"Clinuvel to evaluate SCENESSE® as therapy in vitiligo," Clinuvel announcement (2010).
"UV-protective drug to be tested for vitiligo," Clinuvel announcement (2010).
"FDA allows Clinuvel's innovative vitiligo trial," Clinuvel announcement (2011).
"FDA allows world first vitiligo drug trial," Clinuvel media release (2011).
"Clinuvel Communiqué," Clinuvel newsletter (2011).
"First positive observations from Clinuvel's US vitiligo trial," Clinuvel announcement (2011).
Lim, H.W. et al., "Afamelanotide and narrowband UV-B phototherapy for the treatment of vitiligo. A randomized multicenter trial," JAMA Dermatol. (2014) E1-E9.
U.S. Office Action for U.S. Appl. No. 12/934,024 dated Apr. 9, 2015 (12 pages).
Levine, N. et al., "Induction of skin tanning by subcutaneous administration of a potent synthetic melanotropin," JAMA (1991) 266:2730-2736.
U.S. Office Action for U.S. Appl. No. 12/934,024 dated Dec. 19, 2013 (7 pages).
U.S. Office Action for U.S. Appl. No. 12/934,024 dated May 30, 2014 (8 pages).
Pawelek, J.M., "Approaches to increasing skin melanin with MSH analogs and synthetic melanins," Pigment Cell Research (2001) 14(3):155-160.
Tsukamoto, K. et al., "Approaches to repigmentation of vitiligo skin: new treatment with ultrasonic abrasion, seed-grafting and psoralen plus ultraviolet A therapy," Pigment Cell Research (2002) 15(5):331-334.
International Search Report for Application No. PCT/EP2009/02265 dated Oct. 16, 2009.
Written Opinion for Application No. PCT/EP2009/02265 dated Oct. 16, 2009.
U.S. Office Action for U.S. Appl. No. 12/934,024 dated Jul. 1, 2013.

* cited by examiner

THERAPY FOR VITILIGO

CROSS-REFERENCE TO RELATED APPLICATIONS

This application is a continuation-in-part of Ser. No. 12/934,024, filed on Feb. 8, 2011, which is a U.S. national stage entry of International Patent Application No. PCT/EP2009/002265, filed on Mar. 27, 2009 which claims priority to Australian Patent Application No. 2008901461, filed on Mar. 27, 2008, the contents of all of which are herein fully incorporated by reference.

BRIEF DESCRIPTION OF THE SEQUENCE LISTING

A sequence listing in accordance with 37 C.F.R. par 1.821-1.825 is attached to the present invention and contained in a file named "5120PAF-SEQUENCELISTING-03-13-13.txt" (31,017 bytes, created Mar. 13, 2013) and is incorporated herein by reference.

FIELD OF THE INVENTION

The present invention relates to a therapy for vitiligo. In particular the present invention provides a pharmaceutical composition comprising an alpha melanocyte stimulating hormone (alpha-MSH) analogue either alone or in combination with one or more corticosteroid, immunosuppressant, anti-inflammatory agent and/or photochemotherapeutic agent for the treatment or prevention of vitiligo.

BACKGROUND OF THE INVENTION

Vitiligo is a chronic skin condition that causes loss of pigment, including melanin, resulting in irregular pale patches of skin. The precise etiology of vitiligo is complex and not fully understood although there is some evidence to suggest it is caused by a combination of auto-immune, genetic and environmental factors.

As many as 50% of people with vitiligo develop patches of de-pigmented skin appearing on extremities before their 20s. The patches may grow or remain constant in size and often occur symmetrically across both sides on the body. Occasionally small areas may repigment as they are "recolonised" by melanocytes and following melanin production and release. The location of vitiligo affected skin changes over time, with some patches re-pigmenting and others becoming affected. In some cases, mild trauma to an area of skin seems to cause new patches, for example, around the ankles (caused by friction with shoes or sneakers). Vitiligo may also be caused by stress factors that affect the immune system, causing the body to react or respond by "eliminating" or gradually loose the ability to produce and release melanin, skin pigment. Further, Vitiligo on the scalp may also affect the colour of the hair leaving white patches or streaks, with similar effects observed for facial and body hair.

There are a number of ways to alter the appearance of vitiligo without addressing its underlying cause. In mild cases, vitiligo patches can be hidden with makeup or other cosmetic solutions. If the affected person is pale-skinned, the patches can be made less visible by avoiding sunlight and the sun tanning of unaffected skin. However, exposure to sunlight may also cause the melanocytes to regenerate to allow the pigmentation to come back to its original colour.

Treatment options include medical treatments, surgical therapies, phototherapy and adjunctive treatments. Pharmaceuticals include topical steroid therapy, topical or oral psoralen phototherapy and depigmentation. Surgical therapies include skin grafts, melanocyte transplantations and micropigmentation or tattooing, while adjunctive therapies include sunscreens and cosmetics.

Despite the fact that many treatment options are available, each suffers from its own disadvantages and inherent limitations. For example, phototherapy involves exposing an individual to narrow band UV-B light (NB-UVB) resulting in skin repigmentation. Although phototherapy provides an effective short-term treatment option, repetitive exposure to NB-UVB light is needed to achieve continuous repigmentation. Further, while the frequency of exposure to NB-UVB light varies from individual to individual, repetitive exposure may result in unwanted side-effects including mild burning, blistering and skin irritations. Foremost, the repetitive treatment by UVB increases the risk of inducing skin malignancies, e.g. squamous cell carcinomas and basal cell carcinomas [Journal of Investigative Dermatology (2005) 124, 505-513; High Levels of Ultraviolet B Exposure Increase the Risk of Non-Melanoma Skin Cancer in Psoralen and Ultraviolet A-Treated Patients] [Mayo Clinics update].

Topical corticosteroid therapy has a reported success rate of up to 56%, however, long-term use of corticosteroids can result in thinning of the skin, stretch marks, and dilation of blood vessels. Further, treatment with oral or topical psoralen plus UVA (PUVA) has proven successful, however, patients need to ingest or apply psoralen before receiving the light treatment, and long term use of oral PUVA for the treatment of psoriasis has been associated with an increased incidence of skin cancer.

While immunomodulator creams are believed to cause repigmentation there is little or no scientific support to back this claim.

A need therefore exists to develop more effective treatments for vitiligo.

SUMMARY OF THE INVENTION

In a first aspect of the present invention there is provided a method for treating or preventing vitiligo in a subject comprising administering to the subject a therapeutically or prophylactically effective amount of an alpha-MSH analogue.

In a second aspect of the present invention there is provided the use of an alpha-MSH analogue for the manufacture of a prophylactic or therapeutic agent for the treatment or prevention of vitiligo in a subject.

In a preferred embodiment the method further comprises administering to the subject one or more agents selected from the group consisting of corticosteroids, immunosuppressants, anti-inflammatory agents and a photochemotherapeutic agents.

In a third aspect of the present invention there is provided a pharmaceutical composition for treating or preventing vitiligo comprising an alpha-MSH analogue and one or more agents selected from the group consisting of corticosteroids, immunosuppressants, anti-inflammatory agents and a photochemotherapeutic agents together with a pharmaceutically acceptable carrier or diluent.

In a fourth aspect of the present invention there is provided a method for treating or preventing vitiligo in a subject comprising administering to the subject a therapeutically or prophylactically effective amount of a pharmaceutical composition according to the third aspect of the invention.

In a fifth aspect of the present invention there is provided the use of an effective amount of a pharmaceutical composition according to the third aspect of the invention for the manufacture of a prophylactic or therapeutic medicament for the treatment or prevention of vitiligo in a subject.

In a sixth aspect of the present invention, there is provided a method for treating or preventing vitiligo in a subject comprising administering to the subject a therapeutically or prophylactically effective amount of an alpha-MSH analogue, further comprising the step of exposing the subject to an effective amount of narrow band ultraviolet B (NB UVB) light.

DETAILED DESCRIPTION OF THE INVENTION

Before the present methods are disclosed and described, it is to be understood that the aspects described below are not limited to specific methods or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a", an and the include plural referents unless the context clearly dictates otherwise. Thus, for example, reference to "a pharmaceutical carrier" includes mixtures of two or more such carriers, and the like.

The terms "optional" or "optionally" as used herein means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value.

Similarly, when values are expressed as approximations, by use of the antecedent "about" it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "contacting" as used herein is meant an instance of exposure by close physical contact of at least one substance to another substance. For example, contacting can include contacting a substance, such as a pharmacologic agent, with a cell. A cell can be contacted with a test compound, for example, an analogue of alpha-MSH, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell.

The terms "prophylactic treatment", "prevention" or "preventing" as used herein mean the administration of an active compound or composition to a subject at risk for an undesirable condition. The condition can include a disease, disorder or reaction, or a predisposition to a disease, disorder or reaction. Prophylactic treatment can range from a reduction in the risk for the condition or of the severity of the condition to the complete prevention of the condition.

The terms "therapeutic treatment" and "treating" mean the administration of an active compound or composition to a subject having an undesirable condition such as a disease, disorder or reaction. Therapeutic treatment can range from reduction in the severity of the condition in the subject to the complete recovery of the subject from the condition.

The term "effective amount and time" as used herein means a therapeutic amount and time needed to achieve the desired result or results, e.g., preventing or treating photosensitivity associated with UVR exposure in a subject.

The term "induce" as used herein means initiating a desired response or result that was not present prior to the induction step. The term "induce" also includes the term "potentiate".

The term "intermittent" as used herein means administering an active compound or composition in a series of discreet doses over a determined period, e.g., a period of sustained release comprising of greater than 24 hours of an alpha-MSH analogue for up to 3 months.

The term "potentiate" as used herein means sustaining a desired response at the same level prior to the potentiating step or increasing the desired response over a period of time.

The term "melanogenesis" as used herein is defined as the ability of a subject to produce melanins by melanin-producing cells, or melanocytes.

The term "epidermal tissue" as used herein includes in particular the skin of a subject.

The invention pertains to methods and compositions for treatment of vitiligo utilising an alpha-MSH analogue.

In a first aspect of the present invention there is provided a method for treating or preventing vitiligo in a subject comprising administering to the subject a therapeutically or prophylactically effective amount of an alpha-MSH analogue.

In a second aspect of the present invention there is provided the use of an alpha-MSH analogue for the manufacture of a prophylactic or therapeutic agent for the treatment or prevention of vitiligo in a subject.

In a preferred embodiment the method further comprises administering to the subject one or more agents selected from the group consisting of corticosteroids, immunosuppressants, anti-inflammatory agents and a photochemotherapeutic agents.

In a third aspect of the present invention there is provided a pharmaceutical composition for treating or preventing vitiligo comprising an alpha-MSH analogue and one or more agents selected from the group consisting of corticosteroids, immunosuppressants, anti-inflammatory agents and a photochemotherapeutic agents together with a pharmaceutically acceptable carrier or diluent.

In a fourth aspect of the present invention there is provided a method for treating or preventing vitiligo in a subject comprising administering to the subject a therapeutically or prophylactically effective amount of a pharmaceutical composition according to the third aspect of the invention.

In a fifth aspect of the present invention there is provided the use of an effective amount of a pharmaceutical composition according to the third aspect of the invention for the manufacture of a prophylactic or therapeutic medicament for the treatment or prevention of vitiligo in a subject.

In a sixth aspect of the present invention, there is provided a method for treating or preventing vitiligo in a subject comprising administering to the subject a therapeutically or prophylactically effective amount of an alpha-MSH analogue, further comprising the step of exposing the subject to an effective amount of narrow band ultraviolet B (NB UVB) light.

Preferably the subject is a human or domestic animal subject. Most preferably the subject is a human subject.

It is also preferred that treatment with the alpha-MSH analogue commences as early as possible following appearance of the condition.

Alpha-MSH is released from UVR exposed keratinocytes in human skin following exposure to ultraviolet radiation. It is understood to act on the melanocortin-1-receptors (MC1R) to, exclusively in melanocytes, induce synthesis of the brownish-black melanin pigment. MC1R are expressed on keratinocytes as well as number of other cells including, but not exclusively, immunological cells such as dendritic/Langerhans cells, neutrophils, microglia and monocytes as well as astrocytes, and endothelial cells.

It has previously been disclosed that a super-potent derivative of alpha-MSH, Nle$^4$-D-Phe$^7$-alpha-MSH, can induce melanin synthesis in human volunteers. Nle$^4$-D-Phe$^7$-alpha-MSH contains two amino acid substitutions and is approximately 10 to 1,000-fold more potent than the native hormone at inducing pigmentation in experimental systems such as the frog skin bioassay or in cultured human keratinocytes.

The term "alpha-MSH analogue" as used herein is defined as a derivative of alpha-MSH which exhibits agonist activity for the melanocortin-1 receptor (MC1R), the receptor to which alpha-MSH binds to initiate the production of melanin within a melanocyte. Such derivatives include derivatives in which (i) one or more amino acid residues are deleted from the native alpha-MSH molecule at the N-terminal end, the C-terminal end, or both; and/or (ii) one or more amino acid residues of the native alpha-MSH molecule are replaced by another natural, non-natural or synthetic amino acid residue; and/or (iii) an intramolecular interaction forms as a cyclic derivative.

The use of any alpha-MSH analogue is contemplated in the methods described herein. Several derivatives of alpha-MSH have been synthesized. In one aspect of the present invention, the alpha-MSH analogues described in U.S. Pat. Nos. 4,457,864, 4,485,039, 4,866,038, 4,918,055, 5,049,547, 5,674,839 and 5,714,576 and U.S. Pat. Nos. 4,918,055 and 5,683,981, which are herein incorporated by reference for their teachings with respect to alpha-MSH analogues and their synthesis thereof, can be used herein.

In one aspect of the present invention, the alpha-MSH analogue may be a compound as disclosed in Australian Patent No. 597630, selected from compounds of the formula:

$$R_1-W-X-Y-Z-R_2$$

wherein
R$_1$ is absent, n-Pentadecanoyl, Ac, 4-phenylbutyrul, Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-NH$_2$; or -Gly-Lys-NH$_2$.

In another aspect, the alpha-MSH analogue maybe selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

The alpha-MSH analogue may be a linear analogue as disclosed in U.S. Pat. No. 5,674,839, selected from the group consisting of:
Ac-Ser-Tyr-Ser-Nle-Glu-His-D-Phe-Arg-Trp-Lys-Gly-Pro-Val-NH$_2$,
Ac-Ser-Tyr-Ser-Nle-Asp-His-D-Phe-Arg-Trp-Lys-Gly-Pro-Val-NH$_2$,
Ac-Nle-Glu-His-D-Phe-Arg-Trp-Lys-Gly-Pro-Val-NH$_2$,
Ac-Nle-Asp-His-D-Phe-Arg-Trp-Lys-Gly-Pro-Val-NH$_2$,
Ac-Nle-Asp-His-D-Phe-Arg-Trp-Gly-NH$_2$,
Ac-Nle-Glu-His-D-Phe-Arg-Trp-Lys-NH$_2$,
Ac-Nle-Asp-His-D-Phe-Arg-Trp-Lys-NH$_2$,
Ac-Nle-Glu-His-D-Phe-Arg-Trp-Orn-NH$_2$,
Ac-Nle-Asp-His-D-Phe-Arg-Trp-Orn-NH$_2$,
Ac-Nle-Glu-His-D-Phe-Arg-Trp-Dab-NH$_2$,
Ac-Nle-Asp-His-D-Phe-Arg-Trp-Dab-NH$_2$,
Ac-Nle-Asp-His-D-Phe-Arg-Trp-Dpr-NH$_2$,
Ac-Nle-Glu-His-Phe-Arg-Trp-Lys-NH$_2$, and
Ac-Nle-Asp-His-Phe-Arg-Trp-Lys-NH$_2$.

The alpha-MSH analogue may also be a cyclic analogue as disclosed in U.S. Pat. No. 5,674,839, selected from the group consisting of:

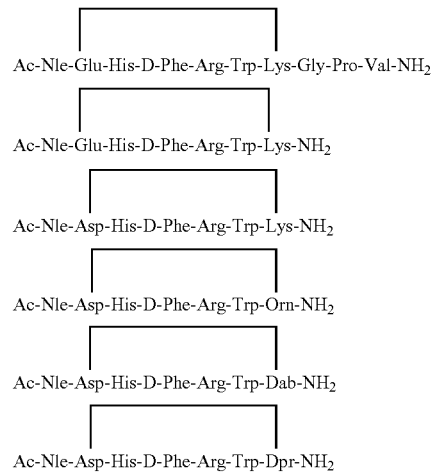

Ac-Ser-Tyr-Ser-Nle-Asp-His-D-Phe-Arg-Trp-Lys-Gly-Pro-Val-NH₂

Ac-Ser-Try-Ser-Nle-Asp-His-D-Phe-Arg-Trp-Lys-NH₂

Ac-Tyr-Ser-Nle-Asp-His-D-Phe-Arg-Trp-Lys-NH₂

Ac-Ser-Nle-Asp-His-D-Phe-Arg-Trp-Lys-NH₂

Ac-Nle-Asp-His-D-Phe-Arg-Trp-Lys-Gly-NH₂

Ac-Nle-Asp-His-D-Phe-Arg-Trp-Lys-Gly-Pro-NH₂

Ac-Nle-Asp-His-D-Phe-Arg-Trp-Lys-Gly-Pro-Val-NH₂, and

Ac-Ser-Nle-Asp-His-D-Phe-Arg-Trp-Lys-Gly-Pro-Val-NH₂, wherein Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO2)Phe=paranitrophenylalanine, Plg=phenylglycine, Pro=proline, Ser=serine, Trp=tryptophan, TrpFor=$N^{1-}$-formyl-tryptophan, Tyr=tyrosine, Val=valine.

All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect of the present invention, the alpha-MSH analogue can be

[D-Phe⁷]-alpha-MSH, [Nle⁴, D-Phe⁷]-alpha-MSH,
[D-Ser¹, D-Phe⁷]-alpha-MSH, [D-Tyr², D-Phe⁷]-alpha-MSH,
[D-Ser³, D-Phe⁷]-alpha-MSH, [D-Met⁴, D-Phe⁷]-alpha-MSH,
[D-Glu⁵, D-Phe⁷]-alpha-MSH, [D-His⁶, D-Phe⁷]-alpha-MSH,
[D-Phe⁷, D-Arg⁸]-alpha-MSH, [D-Phe⁷, D-Trp⁹]-alpha-MSH,
[D-Phe⁷, D-Lys¹¹]-alpha-MSH, [D-Phe⁷, D-Pro¹²]-alpha-MSH,
[D-Phe⁷, D-Val¹³]-alpha-MSH, [D-Ser¹, Nle⁴, D-Phe⁷]-alpha-MSH,
[D-Tyr², Nle⁴, D-Phe⁷]-alpha-MSH,
[D-Ser³, Nle⁴, D-Phe⁷]-alpha-MSH,
[Nle⁴, D-Glu⁵, D-Phe⁷]-alpha-MSH,
[Nle⁴, D-His⁶, D-Phe⁷]-alpha-MSH,
[Nle⁴, D-Phe⁷, D-Arg⁸]-alpha-MSH,
[Nle⁴, D-Phe⁷, D-Trp⁹]-alpha-MSH,
[Nle⁴, D-Phe⁷, D-Lys¹¹]-alpha-MSH,
[Nle⁴, D-Phe⁷, D-Pro¹²]-alpha-MSH,
[Nle⁴, D-Phe⁷, D-Val¹³]-alpha-MSH,

[Cys⁴, Cys¹⁰]-alpha-MSH [Cys⁴, D-Phe⁷, Cys¹⁰]-alpha-MSH

[Cys⁴, Cys¹¹]-alpha-MSH [Cys⁵, Cys¹⁰]-alpha-MSH

[Cys⁵, Cys¹¹]-alpha-MSH [Cys⁴, Cys¹⁰]-alpha-MSH₄₋₁₃

[Cys⁴, Cys¹⁰]-alpha-MSH₄₋₁₂ [Nle⁴, D-Phe⁷]-alpha-MSH₄₋₁₀,
[Nle⁴, D-Phe⁷]-alpha-MSH₄₋₁₁, [D-Phe⁷]-alpha-MSH₅₋₁₁,
[Nle⁴, D-Tyr⁷]-alpha-MSH₄₋₁₁, [(pNO₂)D-Phe⁷]-alpha-MSH₄₋₁₁,
[Tyr⁴, D-Phe⁷]-alpha-MSH₄₋₁₀, [Tyr⁴, D-Phe⁷]-alpha-MSH₄₋₁₁,
[Nle⁴]-alpha-MSH₄₋₁₁, [Nle⁴, (pNO₂)D-Phe⁷]-alpha-MSH₄₋₁₁,
[Nle⁴, D-His⁶]-alpha-MSH₄₋₁₁,
[Nle⁴, D-His⁶, D-Phe⁷]-alpha-MSH₄₋₁₁,
[Nle⁴, D-Arg⁸]-alpha-MSH₄₋₁₁, [Nle⁴, D-Trp⁹]-alpha-MSH₄₋₁₁,
[Nle⁴, D-Phe⁷, D-Trp⁹]-alpha-MSH₄₋₁₁,
[Nle⁴, D-Phe⁷]-alpha-MSH₄₋₉, and
[Nle⁴, D-Phe⁷, D-Trp⁹]-alpha-MSH₄₋₉.

In a further aspect, the alpha-MSH analogue is:
[Nle⁴, D-Phe⁷]-alpha-MSH₄₋₁₀,
[Nle⁴, D-Phe⁷]-alpha-MSH₄₋₁₁,
[Nle⁴, D-Phe⁷, D-Trp⁹]-alpha-MSH₄₋₁₁, or
[Nle⁴, D-Phe⁷]-alpha-MSH₄₋₉.

In a particularly preferred aspect, the alpha-MSH analogue is [Nle⁴, D-Phe⁷]-alpha-MSH.

The pharmaceutical composition according to the first aspect of the invention further comprises one or more agents selected from the group consisting of corticosteroids, immunosuppressants, anti-inflammatory agents and photochemotherapeutic agents.

The corticosteroid according to the invention may be selected from the group consisting of mometasone furoate, betamethasone, dexamethasone, hydrocortisone, methylprednisolone. prednisolone and cortisone. It is particularly preferred that the corticosteroid is mometasone furoate or betamethasone.

The immunosuppressant according to the invention may be selected from the group consisting of cytostatics including cytotoxic antibiotics, alkylating agents and antimetabolites, antibodies, glucocorticoids, drugs acting on immunophilins including cyciosporine, tacrolimus and sirolimus, interferons, azathioprine, 5-fluorouracil and opioids. It is particularly preferred that the immunosuppressant is selected from the group consisting of tacrolimus, betamethasone, azathioprine and levamisole.

The anti-inflammatory agent according to the invention may be selected from the group consisting of betamethasone, cortisone. It is particularly preferred that the anti-inflammatory agent is betamethasone or cortisone.

It is preferred that the photochemotherapeutic agent according to the invention is psoralen.

As will be appreciated by a person skilled in the art, corticosteroids according to the invention may act as an immunosuppressant and/or anti-inflammatory agent. For example, the dipropionate salt of betamethasone (trade name Diprosone) is a glucocorticoid which acts as both an immunosuppressant and an anti-inflammatory agent.

In a second aspect of the present invention there is provided a method for treating or preventing vitiligo in a subject comprising administering to the subject a therapeutically or prophylactically effective amount of a pharmaceutical composition according to the first aspect of the invention.

In a preferred embodiment, the method according to the second aspect of the invention further comprises the step of exposing the subject to an effective amount of ultra-violet A light (UVA) when the pharmaceutical composition administered to the subject comprises one or more photochemotherapeutic agents.

It is known to persons skilled in the art that photochemotherapeutic agents such as psoralens make the skin sensitive to ultra-violet (UV) light, particularly the long wavelength UVA light. Administration of psoralen prior to UVA exposure is known to be effective for treating vitiligo.

Accordingly in a preferred aspect of the present invention the pharmaceutical composition is administered to the subject prior to exposure to UVA light.

In a sixth aspect of the present invention, there is provided a method for treating or preventing vitiligo in a subject comprising administering to the subject a therapeutically or prophylactically effective amount of an alpha-MSH analogue, further comprising the step of exposing the subject to an effective amount of UV light, preferably UVB, more preferably narrow band ultraviolet B (NB UVB) light.

Preferably, the subject is treated with a combination of NB UVB light and alpha-MSH analogue. Preferably the invention is directed to at least partially exposing the subject to the NB UVB light and simultaneously to the alpha-MSH analogue. During exposure to the alpha MSH analogue, the subject is preferably exposed to NB UVB light treatment. This results in exposure to the combination at the same time. In other words, the subject is preferably at least partially treated with NB UVB light while being exposed to the alpha MSH analogue, i.e. the subject is at least partially simultaneously exposed to both. Preferably, exposure of the subject to NB UVB light at least partially overlaps with exposure to the alpha-MSH analogue.

The period of the combination treatment is at least 2 months, more preferably at least 3 months, most preferably at least 4 months and preferably at most 12 months, more preferably at most 7 months. A preferred example is 3 months. Another preferred example is 4 months. Another preferred example is 6 months. Another preferred example is 7 months.

Preferably, the subject is treated with NB UVB light before exposure to the alpha MSH analogue and preferably for a period of at least 1 week, more preferably at least 2 weeks, most preferably at least one month and preferably up to 12 months. This may be called a NB UVB pre-combination-treatment step.

Preferably, the subject is treated with NB UVB light after exposure to the alpha MSH analogue and preferably for a period of at least 1 week, more preferably at least 2 weeks, most preferably at least one month, in particular at least 5 weeks and even more particular at least 6 weeks and preferably up to 24 months. This may be called a NB UVB post-combination-treatment step.

The present invention preferably uses UVB light treatment. UVB treatment may use Broad Band UVB (BB UVB using wavelengths of from 280 to 330 nm) but preferably uses narrow band UVB (NB UVB). Preferably, NB-UVB light treatment uses a wavelength of from 308 to 315 nm, preferably of from 310 to 312 nm, more preferably 311 nm. Preferably, at least 40% of the irradiation (in terms of $W/cm^2$) is within these ranges, more preferably at least 60%, most preferably at least 80%. A further NB-UVB option is the use of a 308 nm xenon-chloride excimer laser. Preferably, the UV irradiance of the spectrum below 300 nm is less than 50% (in $W/cm^2$) of the total irradiance of the UVB light, more preferably less than 20%, most preferably less than 5% of the UVB light. This way most unwanted side-effects of repetitive UVB treatment may be avoided.

Preferably, irradiation is at least 150 $mJ/cm^2$ and preferably at most 3000 $ml/cm^2$. Preferably irradiation level of the next treatment is based on the erythema occurring in the previous UVB treatment. Preferably, the dose is increased by up to 15% or decreased by up to 10%. Depending on any erythema formation of the previous treatment, the dose is preferably increased by 10-15% if no erythema occurred; the dose is kept the same if minimal erythema occurred; or the dose is reduced by 5-10% if mild to moderate erythema occurred. In this last instance, the treating doctor may decide not to give a dose given and in the next treatment either use the last tolerated dose or the scheduled dose.

Preferably, NB UVB treatment takes less than 20 minutes, more preferably less than 10 minutes. NB-UVB is preferably used for less than 6 minutes, for instance maximum 5 minutes.

Preferably, UVB (preferably NB-UVB) light treatment involves repetitive exposure to UVB light. Preferably, the subject is treated with at least 10 NB UVB treatments per month, more preferably twice or thrice weekly. Preferably UVB light treatment occurs on non-consecutive days.

Preferably, the subject is exposed to NB UVB treatment for a period of at least 3 months, more preferably at least 4 most, most preferably at least 5 months, in particularly preferred for a period of at least 6 months and preferably up to 24 months, more preferably 18 months.

Preferred NB-UVB treatment regimen steps are as follows:
1. The subject is exposed for a period of 1 month with thrice weekly NB UVB light of 311 nm with an irradiation of from 150 to 3000 mJ/cm2 for a period of less than 5 minutes.
2. Subsequently, the subject is treated for a period of 4 months with a combination of:
   thrice weekly NB UVB light treatments of 311 nm with an irradiation of from 150 to 3000 mJ/cm2 for a period of 5 minutes;
   monthly administered 16 mg afamelanotide implants, exposing the subject to a level of 0.001 to 10 ng/ml afamelanotide in the blood plasma for a period of from 5 to 10 days; and
3. Then, the subject is exposed for a period of 1 month with thrice weekly NB UVB light of 311 nm with an irradiation of from 150 to 3000 mJ/cm2 for a period of 5 minutes.

In another preferred embodiment, the treatment regimen step 2 takes 3 months. In further preferred embodiment, the treatment regimen step 2 takes 5 months. In further preferred embodiment, the treatment regimen step 2 takes 6 months. In another preferred embodiment, the treatment regimen step 2 takes 7 months.

The alpha MSH analogue for treatment of vitiligo according to the invention is preferably systemically administered by injection. The injection is preferably subcutaneous, intramuscular, intraperitoneal or intravenous. An implant is a preferred example of an injection. Further information on a preferred subcutaneous implant is provided in WO2006/012667 incorporated herein by reference.

A preferred effective amount of the alpha-MSH analogue is represented by the following.

Preferably, the subject is exposed to the alpha MSH analogue at a level of 0.001 ng/ml to 10 ng/ml in the plasma of the subject in the treatment of vitiligo. Preferably, the subject is exposed to the alpha MSH analogue after administration of the alpha-MSH analogue for a period of at least 1 day, more preferably 2 days, most preferably a least 4 days, in particular at least 6 days. Other preferred periods are at least 8 days, more preferably at least 10 days and most preferably at least 12 days.

Preferably, the subject is treated with the alpha-MSH analogue with implants at least weekly, more preferably at least monthly and preferably for a period of at least 2 months, more preferably at least 3 months, most preferably at least 4 months and preferably at most 12 months, more preferably at most 7 months. A preferred example is 3 months. Another preferred example is 4 months. Another preferred example is 6 months. Another preferred example is 7 months.

A preferred embodiment of the invention is a monthly implant comprises from 10 to 25 mg of afamelantoide (preferably 16 mg) that is released over a period of between 7 and 10 days after implantation providing blood plasma levels between 0.001 and 10 ng/ml during this period.

Surprisingly, we have found that the invention is particularly beneficial to subjects with Fitzpatrick skin types III to VI, more preferably IV to VI, and most preferably V to VI. Generally, the darker skin of subjects with higher Fitzpatrick skin types contrasts with pale vitiliginous skin lesions. Even though the darker skin could become darker with treatment providing further contrast, we have found that the difference in skin tone with the vitiliginous patches actually surprisingly decreased over time with treatment according to the invention. Accordingly, the invention preferably relates to subjects with Fitzpatrick skin type III, IV, V or VI, more preferably Fitzpatrick skin type IV, V or VI, most preferably Fitzpatrick skin type VI or VI.

Vitiligo is preferably scored using the VASI (Vitiligo Area Scoring Index) and/or the Vitiligo European Task Force (VETF) scoring systems. These systems have been described in Hamzavi I, et al (2004); "Parametric modeling of narrowband UV-B phototherapy for vitiligo using a novel quantitative took the Vitiligo Area Scoring Index." *Arch Dermatol.* 140(6):677-83; and in Taïeb A, Picardo M & VETF Members (2007). "The definition and assessment of vitiligo: a consensus report of the Vitiligo European Task Force." *Pigment Cell Res.* 20(1):27-35.

The pharmaceutical composition according to the invention may be administered in a sustained-release delivery system as disclosed in International Patent Application No. PCT/AU2005/000181 (WO 2006/012667), or topically using a transdermal delivery system as disclosed in International Patent Application No. PCT/AU2005/001 552 (WO 2006/037188).

It will be appreciated that the actual preferred amounts of the alpha-MSH analogue and corticosteroid, immunosuppressant, anti-inflammatory agent and/or photochemotherapeutic agent (hereinafter referred to as the "active pharmaceutical ingredients") will vary according to the specific compounds being utilized, the particular compositions formulated, the mode of application, and the particular situs and subject being treated. Dosages for a given host can be determined using conventional considerations, e.g. by customary comparison of the differential activities of the subject compounds and of a known agent, e.g. by means of an appropriate conventional pharmacological protocol. Physicians and formulators, skilled in the art of determining doses of pharmaceutical compounds, will have no problems determining doses for prophylactically or therapeutically treating vitiligo by administration of an amount of a pharmaceutical composition of the invention by the methods described herein. In one aspect of the present invention, the pharmaceutical composition is administered in an amount which is effective to prophylactically or therapeutically treat vitiligo.

Any of the alpha-MSH analogues useful herein can be administered to a subject using a variety of administration or delivery techniques known in the art. It is desirable to maintain low concentrations (e.g. concentrations of 0.001 ng to 10 ng/ml) of the alpha-MSH analogue in the plasma of the subject in the treatment of vitiligo. In one preferred embodiment the alpha-MSH analogue is administered in a prolonged release formulation such as described in WO 2006/012667, the disclosure of which is included herein by cross reference. Therefore, the mode of administration will depend upon the subject to be treated and the alpha-MSH analogue selected. In various aspects, the alpha-MSH analogues can be administered orally or parenterally. The term "oral" is used herein to encompass administration of the compounds via the digestive tract. The term "parenteral" is used herein to encompass any route of administration, other than oral administration, by which the alpha-MSH analogue is introduced into the systemic circulation which includes, but is not limited to, intravenous, intramuscular, subcutaneous, intraperitoneal, intradermal, ocular, inhalable, rectal, vaginal, transdermal, topical, buccal, sublingual, or mucosal administration. The term "mucosal" as used herein encompasses the administration of the compounds by methods that employ the mucosa (mucous membranes) of the human body such as, but not limited to, buccal, intranasal, gingival, vaginal, sublingual, pulmonary, or rectal tissue. The term "transdermal" as used herein encompasses the administration of the compounds that go into the skin or go through the skin using formulations such as, but not limited to, transdermal formulations, buccal patches, skin patches, or transdermal patches. The term "topical" as used herein encompasses administration by applying conventional topical preparations such as creams, gels, or solutions for localized percutaneous delivery and/or by solution for systemic and/or localized delivery to areas such as, but not limited to the eye, skin, rectum, and vagina.

In one aspect of the present invention, delivery systems composed of devices or compositions containing an alpha-MSH analogue together with one or more corticosteroid, immunosuppressant, anti-inflammatory agent or photochemotherapeutic agent can be manufactured that allow for the controlled-release, extended-release, modified-release, sustained-release, pulsatile-release, or programmed-release delivery of the active components in order to maintain concentration of the active components in the plasma of the subject.

Depending on the delivery system or composition of a formulation or route of administration chosen, drugs or active pharmaceutical ingredients can be delivered for hours, weeks, or months following a single administration. Drug-delivery devices include, but are not limited to pumps, needle-free injectors, metered-dose inhalers, and the like. Transdermal compositions with or without penetration enhancers include but are not limited to transdermal patches, microneedles, and transdermal formulations that achieve drug delivery using inotophoresis, sonophoresis, electroporation, thermoporation, perfusion, adsorption and absorption. Other delivery systems include, but are not limited to, biodegradable of non-biodegradable rods or other shaped implants, fibers, microparticles, microspheres, microcapsules, nanospheres, nanocapsules, porous silicon nanoparticles, in situ gelling formulations, in situ bolus forming compositions, quick dissolving tablets and the like, buccal patches, films, tablets, capsules, osmotic pressure driven formulations, liquid filled capsules, liposomes and other lipid based compositions and the like, pegalation and the like, hydrogel formulations, emulsions, microemulsions, and suspensions.

In one aspect of the present invention, polymeric delivery systems can be microparticles including, but not limited to microspheres, microcapsules, nanospheres and nanoparticles comprising biodegradable polymeric excipients, non-biodegradable polymeric excipients, or mixtures of polymeric excipients thereof, or the polymeric delivery systems can be, but not limited to rods or other various shaped implants, wafers, fibers, films, in situ forming boluses and the like comprising biodegradable polymeric excipients, non-biodegradable polymeric excipients, or mixtures thereof. These systems can be made from a single polymeric excipient or a mixture or blend of two or more polymeric excipients.

A suitable polymeric excipient includes, but is not limited to, a poly(diene) such as poly(butadiene) and the like; a poly(alkene) such as polyethylene, polypropylene, and the like; a poly(acrylic) such as poly(acrylic acid) and the like; a poly(methacrylic) such as poly(methyl methacrylate), a poly(hydroxyethyl methacrylate), and the like; a poly(vinyl ether); a poly(vinyl alcohol); a poly(vinyl ketone); a poly(vinyl halide) such as poly(vinyl chloride) and the like; a poly(vinyl nitrile), a poly(vinyl ester) such as poly(vinyl acetate) and the like; a poly(vinyl pyridine) such as poly(2-vinyl pyridine), poly(5-methyl-2-vinyl pyridine) and the like; a poly(styrene); a poly(carbonate); a poly(ester); a poly(orthoester) including a copolymer; a poly(esteramide); a poly(anhydride); a poly(urethane); a poly(amide); a cellulose ether such as methyl cellulose, hydroxyethyl cellulose, hydroxypropyl methyl cellulose, and the like; a cellulose ester such as cellulose acetate, cellulose acetate phthalate, cellulose acetate butyrate, and the like; a poly(saccharide), a protein, gelatin, starch, gum, a resin, and the like. These materials may be used alone, as physical mixtures (blends), or as co-polymers. Derivatives of any of the polymers listed above are also contemplated.

In one aspect of the present invention, the polymeric excipient of the delivery system includes a biocompatible, non-biodegradable polymer such as, for example, a silicone, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend or copolymer thereof.

In another aspect, the polymeric excipient includes a biocompatible, biodegradable polymer such as, for example, a poly(lactide); a poly(glycolide); a poly(lactide-co-glycolide); a poly(lactic acid); a poly(glycolic acid); a poly(lactic acid-co-glycolic acid); a poly(caprolactone); a poly(orthoester); a poly(phosphazene); a poly(hydroxybutyrate) or a copolymer containing a poly(hydroxybutarate); a poly(lactide-co-caprolactone); a polycarbonate; a polyesteramide; a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene)copolymer, or a blend or copolymer thereof.

In one aspect of the present invention, the delivery system comprises an implant or rod, wherein the implant or rod comprises a biodegradable polymer, wherein the pharmaceutical composition of the invention is embedded within the implant or rod. In another aspect of the present invention, the pharmaceutical composition of the invention is encapsulated in an implant or rod composed of poly(lactide-co-glycolide), poly(lactide), poly(glycolide), or a mixture thereof. Lactide/glycolide polymers for drug-delivery formulations are typically made by melt polymerization through the ring opening of lactide and glycolide monomers.

Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. In another aspect of the present invention, linear lactide/glycolide polymers are used; however star polymers can be used as well. In certain aspects, high molecular weight polymers can be used for medical devices, for example, to meet strength requirements. In other aspects, low molecular weight polymers can be used for drug-delivery and vaccine delivery products where resorption time and not material strength is as important. The lactide portion of the polymer has an asymmetric carbon. Commercially racemic DL-, L-, and D-polymers are available. The L-polymers are more crystalline and resorb slower than DL-polymers. In addition to copolymers comprising glycolide and DL-lactide or L-lactide, copolymers of L-lactide and DL-lactide are available. Additionally, homopolymers of lactide or glycolide are available.

In the case when the biodegradable polymer is poly(lactide-co-glycolide), poly(lactide), or poly(glycolide), the amount of lactide and glycolide in the polymer can vary. In one aspect of the present invention, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In another aspect of the present invention, the biodegradable polymer can be poly(lactide), 85:15 poly(lactide-co-glycolide), 75:25 poly(lactide-co-glycolide), or 65:35 poly(lactide-co-glycolide) where the ratios are mole ratios.

In one aspect of the present invention, when the biodegradable polymer is poly(lactide-co-glycolide), poly(lactide), or poly(glycolide), the polymer has an intrinsic viscosity of from 0.15 to 1.5 dL/g, 0.25 to 1.5 dL/g, 0.25 to 1.0 dL/g, 0.25 to 0.8 dL/g, 0.25 to 0.6 dL/g, or 0.25 to 0.4 dL/g as measured in chloroform at a concentration of 0.5 g/dL at 30° C.

The amount of alpha-MSH analogue, corticosteroid, immunosuppressant, anti-inflammatory agent and/or photochemotherapeutic agent that is encapsulated or incorporated in the biodegradable polymer will vary depending upon the selection of the biodegradable polymer, the encapsulation or incorporation technique, and the amount of active pharmaceutical ingredients to be delivered to the subject. In one aspect of the present invention, the amount of active pharmaceutical ingredients encapsulated in the microcapsule, implant, or rod can be up to 50% by weight of the delivery system. In other aspects, the amount of active pharmaceutical ingredients encapsulated in the microcapsule, implant, or rod can be from 5 to 60, 10 to 50%, 15 to 40%, or 15 to 30% by weight of the delivery system.

In another aspect, where the alpha-MSH analogue in combination with one or more corticosteroid, immunosuppressant, anti-inflammatory agent or photochemotheapeutic agent is delivered by another delivery system such as a transdermal formulation, the amount of active pharmaceutical ingredients in the formulation can be from 0.001 to 10%, or 0.05 to 5% by weight of the formulation.

Other pharmaceutically acceptable components can be encapsulated or incorporated in the delivery system in combination with the alpha-MSH analogue, corticosteroid, immunosuppressant and/or anti-inflammatory agent. For example, the pharmaceutically acceptable component can include, but is not limited to, a fatty acid, a sugar, a salt, a water-soluble polymer such as polyethylene glycol, a protein, polysaccharide, or carboxmethyl cellulose, a surfactant, a plasticizer, a high- or low-molecular-weight porosigen such as polymer or a salt or sugar, or a hydrophobic low-molecular-weight compound such as cholesterol or a wax. In another aspect, the delivery system comprises an implant or rod, wherein the alpha-MSH analogue is [Nle$^4$, D-Phe$^7$]-alpha-MSH in the amount from 15% to 45% by weight of the implant or rod, wherein the rod or implant comprises poly(lactide) or poly(lactide-co-glycolide) such as, for example, 85:15 poly(lactide-co-glycolide).

Any of the delivery systems described herein can be administered using techniques known in the art. In one aspect of the present invention, the delivery system can be administered subcutaneously to the subject. In this aspect, the duration of administration can vary depending upon the amount of active pharmaceutical ingredients that are encapsulated and the biodegradable polymer selected. In another aspect of the present invention, the delivery system is administered subcutaneously to the subject and releases the active pharmaceutical ingredients for a period of at least 2, 4, 6, 8, 10 or 12 days. In another aspect of the present invention, the delivery system releases the active pharmaceutical ingredients in the subject for at least 1, 2 or 3 months. In various other aspects, the delivery system releases the active pharmaceutical ingredients in the subject for 10 days, 15 days, 20 days, 25 days, or 30 days.

In a preferred embodiment of the present invention the pharmaceutical composition is administered to a subject when skin lesions are active. The term "active lesion" as used herein means incipient vitiligo lesions of the skin, or incipient loss of pigmentation of the skin, migrating areas of depigmentation of the skin. Active lesions show clinically daily, weekly and monthly pigmentation ('discolouring') changes over time.

The pharmaceutical compositions can be prepared using techniques known in the art. In one aspect of the present invention, the composition is prepared by admixing the alpha-MSH analogue and corticosteroid, immunosuppressant and/or anti-inflammatory agent with a pharmaceutically-acceptable carrier. The term "admixing" is defined as mixing the two components together so that there is no chemical reaction or physical interaction. The term "admixing" also includes the chemical reaction or physical interaction between the alpha-MSH analogue, corticosteroid, immunosuppressant and/or anti-inflammatory agent and the pharmaceutically-acceptable carrier.

Pharmaceutically-acceptable carriers are known to those skilled in the art. These most typically would be standard earners for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include, ointments, lotions, creams, gels, drops, ointments, suppositories, sprays, liquids and powders. Conventional pharmaceutical carriers, aqueous, powder or oily bases, thickeners and the like may be necessary or desirable. The active pharmaceutical ingredients can be admixed under sterile conditions with a physiologically acceptable carrier and any preservatives, buffers, propellants, or absorption enhancers as may be required or desired. Reference is made to documents cited herein, e.g., U.S. Pat. No. 5,990,091, WO 98/00166, and WO 99/60164, for the preparation of compositions for topical applications, e.g., viscous compositions that can be creams or ointments, as well as compositions for nasal and mucosal administration.

In the case when the composition is administered mucosally, ocularly, intranasally, or by inhalation, the formulation can be in the form of a drop, a spray, an aerosol, or a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss.

In a preferred embodiment of the present invention the pharmaceutical composition according is administered to a human or domestic animal subject. Most preferably the subject is a human subject.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Example

Patients suffering from vitiligo were recruited in a trial investigating the efficacy of afamelanotide (Scenesse) in combination with NB-UVB in comparison with NB-UVB monotherapy. dult subjects with stable or slowly progressive vitiligo of 15-50% of total body depigmentation and with Fitzpatrick skin types III-VI were included. Patients were diagnosed with vitiligo within the past five years of study commencement and had not received NB-UVB treatment within six months of the screening visit.

Fifty-four patients were randomly assigned in equal numbers to one of the two treatment groups. Group A (active) received one month of thrice weekly NB-UVB monotherapy, followed by monthly doses of SCENESSE® (one 16 mg afamelanotide implant administered underneath the skin as a dissolvable implant on study days 28, 56, 84 and 112) in with combination thrice weekly NB-UVB therapy for four months, and then a final month of thrice weekly NB-UVB monotherapy. Group A patients received a total of 72 NB-UVB treatments over the course of the 6 month period. Group B (placebo) received thrice weekly NB-UVB monotherapy for six months, for a total of 72 NB-UVB treatments over the course of the 6 month period.

NB-UVB light of 311 nm was used on the entire body for a maximum of 6 minutes, three times a week on non-consecutive days for the 6 month study period with a required minimum number of 10 NB-UVB treatments per month. NB-UVB treatment was started at the same fixed dose of 150 ml/cm$^2$. A maximum of 3 J/cm$^2$ was used. For the following treatment, the dose could be adjusted as follows: the dose could be increased with 10-15% compared to the previous dose (if no erythema occurred), kept the same (if minimal erythema occurred following the previous treatment), or reduced with 5-10% (if the mild to moderate erythema occurred).

Efficacy was measured using the Vitiligo Area Scoring Index (VASI) and standardized Vitiligo European Task Force (VETF) scores between day 0 and day 168. The VASI is a validated measure to assess the extent of vitiligo involvement in patients; the VETF score equally measures skin surface to assess the areas affected by vitiligo. Speed of repigmentation, depth of repigmentation, stability of pigmentation, and safety of combination therapy were recorded.

Forty-one (75.9%, n=41) patients completed the treatment. Thirteen patients withdrew due to their inability to comply with the demanding treatment protocol, or, in the case of five patients, due to the intensity of pigmentation experienced.

The extent of repigmentation in the SCENESSE®/NB-UVB group was significantly greater than observed in the NB-UVB-alone group (VASI, p=0.025; VETF p=0.023; 95% CI).

Significantly better, more complete and deeper repigmentation was observed for those patients with the darkest skin complexion having Fitzpatrick skin type IV to VI (n=24) who had received the combination therapy in comparison with those patients on monotherapy (p=0.046; 95% CI).

The VASI scores showed that those patients who had received the combination therapy achieved earlier repigmentation than those on monotherapy (median time 43 days versus 68 days, p=0.086; 95% CI).

Overall the combined treatment was well tolerated and no serious drug-related adverse events were reported.

It can be concluded that the proposed combination therapy of NB-UVB with SCENESSE® enables a faster and more complete repigmentation for people with vitiligo. After combination treatment with NB-UVB light treatment led to excellent maintenance of repigmentation. Patients with Fitzpatrick skin types IV, V and VI responded especially well to treatment. This is particularly interesting as vitiligo tends to be most visible for these patients. Overall, the feedback from patients and physicians has been very positive.

EMBODIMENTS

Embodiment 1

A pharmaceutical composition for treating or preventing vitiligo comprising an alpha-MSH analogue selected from compounds of the formula:

R$_1$—W—X—Y—Z—R$_2$

Wherein
R$_1$ is absent, n-Pentadecanoyl, Ac, 4-phenylbutyrul, Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-NH$_2$; or -Gly-Lys-NH$_2$.

Embodiment 2

A pharmaceutical composition for treating or preventing vitiligo comprising a linear alpha-MSH analogue selected from the group consisting of:
Ac-Ser-Tyr-Ser-Nle-Glu-His-D-Phe-Arg-Trp-Lys-Gly-Pro-Val-NH$_2$,
Ac-Ser-Tyr-Ser-Nle-Asp-His-D-Phe-Arg-Trp-Lys-Gly-Pro-Val-NH$_2$,
Ac-Nle-Glu-His-D-Phe-Arg-Trp-Lys-Gly-Pro-Val-NH$_2$,
Ac-Nle-Asp-His-D-Phe-Arg-Trp-Lys-Gly-Pro-Val-NH$_2$,
Ac-Nle-Asp-His-D-Phe-Arg-Trp-Gly-NH$_2$,
Ac-Nle-Glu-His-D-Phe-Arg-Trp-Lys-NH$_2$,
Ac-Nle-Asp-His-D-Phe-Arg-Trp-Lys-NH$_2$,
Ac-Nle-Glu-His-D-Phe-Arg-Trp-Orn-NH$_2$,
Ac-Nle-Asp-His-D-Phe-Arg-Trp-Orn-NH$_2$,
Ac-Nle-Glu-His-D-Phe-Arg-Trp-Dab-NH$_2$,
Ac-Nle-Asp-His-D-Phe-Arg-Trp-Dab-NH$_2$,
Ac-Nle-Asp-His-D-Phe-Arg-Trp-Dpr-NH$_2$,
Ac-Nle-Glu-His-Phe-Arg-Trp-Lys-NH$_2$,
Ac-Nle-Asp-His-Phe-Arg-Trp-Lys-NH$_2$,
or a cyclic alpha-MSH analogue selected from the group consisting of:

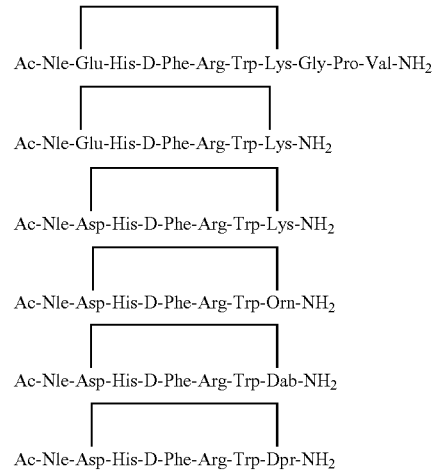

-continued

Ac-Ser-Tyr-Ser-Nle-Asp-His-D-Phe-Arg-Trp-Lys-Gly-Pro-Val-NH$_2$

Ac-Ser-Try-Ser-Nle-Asp-His-D-Phe-Arg-Trp-Lys-NH$_2$

Ac-Tyr-Ser-Nle-Asp-His-D-Phe-Arg-Trp-Lys-NH$_2$

Ac-Ser-Nle-Asp-His-D-Phe-Arg-Trp-Lys-NH$_2$

Ac-Nle-Asp-His-D-Phe-Arg-Trp-Lys-Gly-NH$_2$

Ac-Nle-Asp-His-D-Phe-Arg-Trp-Lys-Gly-Pro-NH$_2$

Ac-Nle-Asp-His-D-Phe-Arg-Trp-Lys-Gly-Pro-Val-NH$_2$

Ac-Ser-Nle-Asp-His-D-Phe-Arg-Trp-Lys-Gly-Pro-Val-NH$_2$, wherein Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO2)Phe=paranitrophenylalanine, Plg=phenylglycine, Pro=proline, Ser=serine, Trp=tryptophan, TrpFor=N$^{1-}$-formyl-tryptophan, Tyr=tyrosine, Val=valine.

Embodiment 3

A pharmaceutical composition for treating or preventing vitiligo comprising an alpha-MSH analogue selected from the group consisting of:

[D-Phe$^7$]-alpha-MSH, [Nle$^4$, D-Phe$^7$]-alpha-MSH,
[D-Ser$^1$, D-Phe$^7$]-alpha-MSH, [D-Tyr$^2$, D-Phe$^7$]-alpha-MSH,
[D-Ser$^3$, D-Phe$^7$]-alpha-MSH, [D-Met$^4$, D-Phe$^7$]-alpha-MSH,
[D-Glu$^5$, D-Phe$^7$]-alpha-MSH, [D-His$^6$, D-Phe$^7$]-alpha-MSH,
[D-Phe$^7$, D-Arg$^8$]-alpha-MSH, [D-Phe$^7$, D-Trp$^9$]-alpha-MSH,
[D-Phe$^7$, D-Lys$^{11}$]-alpha-MSH, [D-Phe$^7$, D-Pro$^{12}$]-alpha-MSH,
[D-Phe$^7$, D-Val$^{13}$]-alpha-MSH, [D-Ser$^1$, Nle$^4$, D-Phe$^7$]-alpha-MSH,
[D-Tyr$^2$, Nle$^4$, D-Phe$^7$]-alpha-MSH,
[D-Ser$^3$, Nle$^4$, D-Phe$^7$]-alpha-MSH,
[Nle$^4$, D-Glu$^5$, D-Phe$^7$]-alpha-MSH,
[Nle$^4$, D-His$^6$, D-Phe$^7$]-alpha-MSH,
[Nle$^4$, D-Phe$^7$, D-Arg$^8$]-alpha-MSH,
[Nle$^4$, D-Phe$^7$, D-Trp$^9$]-alpha-MSH,
[Nle$^4$, D-Phe$^7$, D-Lys$^{11}$]-alpha-MSH,
[Nle$^4$, D-Phe$^7$, D-Pro$^{12}$]-alpha-MSH,
[Nle$^4$, D-Phe$^7$, D-Val$^{13}$]-alpha-MSH,

[Cys$^4$, Cys$^{10}$]-alpha-MSH [Cys$^4$, D-Phe$^7$, Cys$^{10}$]-alpha-MSH

[Cys$^4$, Cys$^{11}$]-alpha-MSH [Cys$^5$, Cys$^{10}$]-alpha-MSH

[Cys$^5$, Cys$^{11}$]-alpha-MSH [Cys$^4$, Cys$^{10}$]-alpha-MSH$_{4-13}$

[Cys$^4$, Cys$^{10}$]-alpha-MSH$_{4-12}$ [Nle$^4$, D-Phe$^7$]-alpha-MSH$_{4-10}$,
[Nle$^4$, D-Phe$^7$]-alpha-MSH$_{4-11}$, [D-Phe$^7$]-alpha-MSH$_{5-11}$,
[Nle$^4$, D-Tyr$^7$]-alpha-MSH$_{4-11}$, [(pNO$_2$)D-Phe$^7$]-alpha-MSH$_{4-11}$,
[Tyr$^4$, D-Phe$^7$]-alpha-MSH$_{4-10}$, [Tyr$^4$, D-Phe$^7$]-alpha-MSH$_{4-11}$,
[Nle$^4$]-alpha-MSH$_{4-11}$, [Nle$^4$, (pNO$_2$)D-Phe$^7$]-alpha-MSH$_{4-11}$,
[Nle$^4$, D-His$^6$]-alpha-MSH$_{4-11}$,
[Nle$^4$, D-His$^6$, D-Phe$^7$]-alpha-MSH$_{4-11}$,
[Nle$^4$, D-Arg$^8$]-alpha-MSH$_{4-11}$, [Nle$^4$, D-Trp$^9$]-alpha-MSH$_{4-11}$,
[Nle$^4$, D-Phe$^7$, D-Trp$^9$]-alpha-MSH$_{4-11}$,
[Nle$^4$, D-Phe$^7$]-alpha-MSH$_{4-9}$, or
[Nle$^4$, D-Phe$^7$, D-Trp$^9$]-alpha-MSH$_{4-9}$.

Embodiment 4

A pharmaceutical composition for treating or preventing vitiligo comprising an alpha-MSH analogue selected from the group consisting of:

[Nle$^4$, D-Phe$^7$]-alpha-MSH$_{4-10}$,
[Nle$^4$, D-Phe$^7$]-alpha-MSH$_{4-11}$,
[Nle$^4$, D-Phe$^7$, D-Trp$^9$]-alpha-MSH$_{4-11}$,
[Nle$^4$, D-Phe$^7$]-alpha-MSH$_{4-9}$.

Embodiment 5

A pharmaceutical composition for treating or preventing vitiligo comprising an alpha-MSH analogue selected from the group consisting of:
[Nle$^4$, D-Phe$^7$]-alpha-MSH.

Embodiment 6

The pharmaceutical composition according to embodiments 1 to 5, further comprising one or more agents selected from the group consisting of corticosteroids, immunosuppressants, anti-inflammatory agents and photochemotherapeutic agents together with a pharmaceutically acceptable carrier or diluent.

Embodiment 7

The pharmaceutical composition according to embodiment 6, wherein the corticosteroid is selected from mometasone furoate, betamethasone, dexamethasone, hydrocortisone, methylprednisolone, prednisolone and cortisone.

Embodiment 8

The pharmaceutical composition according to embodiment 6, wherein the corticosteroid is selected from mometasone furoate and betamethasone.

Embodiment 9

The pharmaceutical composition according to embodiment 6, wherein the immunosuppressant is selected from cytostatics including cytotoxic antibiotics, alkylating agents and antimetabolites, antibodies, glucocorticoids, drugs acting on immunophilins including cyclosporine, tacrolimus and sirolimus, interferons, azathioprine, 5-fluorouracil and opioids.

Embodiment 10

The pharmaceutical composition according to embodiment 6, wherein the immunosuppressant is selected from tacrolimus, betamethasone, azathioprine and levamisole.

Embodiment 11

The pharmaceutical composition according to embodiment 6, wherein the anti-inflammatory agent is selected from betamethasone and cortisone.

Embodiment 12

The pharmaceutical composition according to embodiment 6, wherein the photochemotherapeutic agent is psoralen.

Embodiment 13

A method for treating or preventing vitiligo in a subject comprising administering to the subject a therapeutically or prophylactically effective amount of a pharmaceutical composition comprising an alpha-MSH analogue according to embodiments 1 to 12.

Embodiment 14

The method according to embodiment 13, further comprising the step of exposing the subject to an effective amount of ultra-violet light (UV), in particular ultra-violet A light (UVA), when the pharmaceutical composition administered to the subject comprises one or more photochemotherapeutic agents.

Embodiment 15

The method according to embodiments 13 or 14, wherein the pharmaceutical composition is administered in a sustained-release delivery system, topically using a transdermal delivery system or in a prolonged release formulation.

Embodiment 16

The method according to embodiments 13 to 15, wherein the concentration of the alpha-MSH analogue in the plasma of the subject in the treatment of vitiligo is maintained in a low concentration range of 0.001 ng/ml to 10 ng/ml.

Embodiment 17

The method according to embodiments 13 to 16, wherein the pharmaceutical composition is administered orally or parenterally.

Embodiment 18

A delivery system composed of devices or compositions containing an alpha-MSH analogue together with one or more corticosteroids, immunosuppressants, anti-inflammatory agents or photochemotherapeutic agents according to embodiments 1 to 12, wherein the delivery system allows for the controlled-release, extended-release, modified-release, sustained-release, pulsatile-release, or programmed-release delivery of the active components in order to maintain concentration of the active components in the plasma of the subject.

The invention claimed is:

1. A method for treating vitiligo in a subject in need thereof comprising subcutaneously administering to the subject a therapeutically-effective amount of an alpha-MSH analogue, wherein the alpha-MSH analogue is administered in a sustained release composition comprising poly(lactide-co-glycolide), wherein the alpha-MSH analogue is [Nle$^4$, D-Phe$^7$]-alpha-MSH, and further comprising the step of exposing the subject to an effective amount of narrow band ultraviolet B (NB-UVB) light.

2. The method according to claim 1, wherein the subject is exposed to NB-UVB light treatment and to alpha-MSH analogue at the same time.

3. The method according to claim 1, wherein the subject is exposed to NB-UVB light treatment during a period of at least 1 week before administration of the alpha-MSH analogue.

4. The method according to claim 1, wherein the subject is exposed to NB-UVB light treatment during a period of at least 1 week after administration of the alpha-MSH analogue.

5. The method according to claim 1, wherein the subject has Fitzpatrick skin type IV, V or VI.

6. The method according to claim 1, wherein the alpha-MSH analogue is present in the blood plasma of the subject at a concentration of from 0.001 ng/ml to 10 ng/ml for a period of at least 2 days.

7. The method according to claim 1, wherein the alpha-MSH analogue is administered in a composition further comprising one or more agents selected from the group consisting of corticosteroids, immunosuppressants, anti-inflammatory agents and photochemotherapeutic agents together with a pharmaceutically acceptable carrier or diluent.

8. The method according to claim 1, wherein the sustained release composition maintains a plasma concentration in the subject of 0.001 to 10 ng/ml.

9. The method according to claim 1, wherein the sustained release composition releases the alpha-MSH analogue for a period of at least 2 days.

* * * * *

SEQUENCE LISTING

```
<160> NUMBER OF SEQ ID NOS: 74

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: misc_feature
<222> LOCATION: (13)..(13)
<223> OTHER INFORMATION: C-term amidated

<400> SEQUENCE: 1

Ser Tyr Ser Leu Glu His Phe Arg Trp Lys Gly Pro Val
1               5                   10

<210> SEQ ID NO 2
```

-continued

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: misc_feature
<222> LOCATION: (13)..(13)
<223> OTHER INFORMATION: C-term amidated

<400> SEQUENCE: 2

Ser Tyr Ser Leu Asp His Phe Arg Trp Lys Gly Pro Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (10)..(10)
<223> OTHER INFORMATION: C-term amidated

<400> SEQUENCE: 3

Leu Glu His Phe Arg Trp Lys Gly Pro Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
```

```
<221> NAME/KEY: misc_feature
<222> LOCATION: (10)..(10)
<223> OTHER INFORMATION: C-term amidated

<400> SEQUENCE: 4

Leu Asp His Phe Arg Trp Lys Gly Pro Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 5

Leu Asp His Phe Arg Trp Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 6

Leu Glu His Phe Arg Trp Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

-continued

```
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 7

Leu Asp His Phe Arg Trp Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn
<220> FEATURE:
<221> NAME/KEY: misc_feature
<222> LOCATION: (7)..(7)
<223> OTHER INFORMATION: C-term amidated

<400> SEQUENCE: 8

Leu Glu His Phe Arg Trp Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn
<220> FEATURE:
```

```
<221> NAME/KEY: misc_feature
<222> LOCATION: (7)..(7)
<223> OTHER INFORMATION: C-term amidated

<400> SEQUENCE: 9

Leu Asp His Phe Arg Trp Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab
<220> FEATURE:
<221> NAME/KEY: misc_feature
<222> LOCATION: (7)..(7)
<223> OTHER INFORMATION: C-term amidated

<400> SEQUENCE: 10

Leu Glu His Phe Arg Trp Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab
<220> FEATURE:
<221> NAME/KEY: misc_feature
<222> LOCATION: (7)..(7)
<223> OTHER INFORMATION: C-term amidated

<400> SEQUENCE: 11

Leu Asp His Phe Arg Trp Xaa
1               5

<210> SEQ ID NO 12
```

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dpr
<220> FEATURE:
<221> NAME/KEY: misc_feature
<222> LOCATION: (7)..(7)
<223> OTHER INFORMATION: C-term amidated

<400> SEQUENCE: 12

Leu Glu His Phe Arg Trp Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (7)..(7)
<223> OTHER INFORMATION: C-term amidated

<400> SEQUENCE: 13

Leu Glu His Phe Arg Trp Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (7)..(7)
<223> OTHER INFORMATION: C-term amidated
```

```
<400> SEQUENCE: 14

Leu Asp His Phe Arg Trp Lys
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (10)..(10)
<223> OTHER INFORMATION: C-term amidated

<400> SEQUENCE: 15

Leu Glu His Phe Arg Trp Lys Gly Pro Val
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 16

Leu Glu His Phe Arg Trp Lys
1               5

<210> SEQ ID NO 17
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 17

Leu Asp His Phe Arg Trp Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn
<220> FEATURE:
<221> NAME/KEY: misc_feature
<222> LOCATION: (7)..(7)
<223> OTHER INFORMATION: C-term amidated

<400> SEQUENCE: 18

Leu Asp His Phe Arg Trp Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
```

```
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dab
<220> FEATURE:
<221> NAME/KEY: misc_feature
<222> LOCATION: (7)..(7)
<223> OTHER INFORMATION: C-term amidated

<400> SEQUENCE: 19

Leu Asp His Phe Arg Trp Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Dpr
<220> FEATURE:
<221> NAME/KEY: misc_feature
<222> LOCATION: (7)..(7)
<223> OTHER INFORMATION: C-term amidated

<400> SEQUENCE: 20

Leu Asp His Phe Arg Trp Xaa
1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (4)..(4)
<223> OTHER INFORMATION: Nle
```

```
<220> FEATURE:
<221> NAME/KEY: misc_feature
<222> LOCATION: (5)..(10)
<223> OTHER INFORMATION: Cyclic
<220> FEATURE:
<221> NAME/KEY: MOD_RES
<222> LOCATION: (7)..(7)
<223> OTHER INFORMATION: D-Phe
<220> FEATURE:
<221> NAME/KEY: misc_feature
<222> LOCATION: (13)..(13)
<223> OTHER INFORMATION: C-term amidated

<400> SEQUENCE: 21

Ser Tyr Ser Leu Asp His Phe Arg Trp Lys Gly Pro Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (5)..(10)
<223> OTHER INFORMATION: Cyclic
<220> FEATURE:
<221> NAME/KEY: MOD_RES
<222> LOCATION: (7)..(7)
<223> OTHER INFORMATION: D-Phe
<220> FEATURE:
<221> NAME/KEY: misc_feature
<222> LOCATION: (10)..(10)
<223> OTHER INFORMATION: C-term amidated

<400> SEQUENCE: 22

Ser Tyr Ser Leu Asp His Phe Arg Trp Lys
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (3)..(3)
<223> OTHER INFORMATION: Nle
<220> FEATURE:
<221> NAME/KEY: misc_feature
<222> LOCATION: (4)..(9)
<223> OTHER INFORMATION: Cyclic
<220> FEATURE:
<221> NAME/KEY: MOD_RES
<222> LOCATION: (6)..(6)
<223> OTHER INFORMATION: D-Phe
<220> FEATURE:
<221> NAME/KEY: misc_feature
<222> LOCATION: (9)..(9)
```

```
<223> OTHER INFORMATION: C-term amidated

<400> SEQUENCE: 23

Tyr Ser Leu Asp His Phe Arg Trp Lys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (2)..(2)
<223> OTHER INFORMATION: Nle
<220> FEATURE:
<221> NAME/KEY: misc_feature
<222> LOCATION: (3)..(8)
<223> OTHER INFORMATION: Cyclic
<220> FEATURE:
<221> NAME/KEY: MOD_RES
<222> LOCATION: (5)..(5)
<223> OTHER INFORMATION: D-Phe
<220> FEATURE:
<221> NAME/KEY: misc_feature
<222> LOCATION: (8)..(8)
<223> OTHER INFORMATION: C-term amidated

<400> SEQUENCE: 24

Ser Leu Asp His Phe Arg Trp Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (7)..(7)
<223> OTHER INFORMATION: C-term amidated

<400> SEQUENCE: 25

Leu Asp His Phe Arg Trp Lys
1               5

<210> SEQ ID NO 26
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (8)..(8)
<223> OTHER INFORMATION: C-term amidated

<400> SEQUENCE: 26

Leu Asp His Phe Arg Trp Lys Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (9)..(9)
<223> OTHER INFORMATION: C-term amidated

<400> SEQUENCE: 27

Leu Asp His Phe Arg Trp Lys Gly Pro
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (1)..(1)
```

```
<223> OTHER INFORMATION: Nle
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Phe
<220> FEATURE:
<221> NAME/KEY: misc_feature
<222> LOCATION: (10)..(10)
<223> OTHER INFORMATION: C-term amidated

<400> SEQUENCE: 28

Leu Asp His Phe Arg Trp Lys Gly Pro Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (2)..(2)
<223> OTHER INFORMATION: Nle
<220> FEATURE:
<221> NAME/KEY: misc_feature
<222> LOCATION: (3)..(8)
<223> OTHER INFORMATION: Cyclic
<220> FEATURE:
<221> NAME/KEY: MOD_RES
<222> LOCATION: (5)..(5)
<223> OTHER INFORMATION: D-Phe
<220> FEATURE:
<221> NAME/KEY: misc_feature
<222> LOCATION: (11)..(11)
<223> OTHER INFORMATION: C-term amidated

<400> SEQUENCE: 29

Ser Leu Asp His Phe Arg Trp Lys Gly Pro Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe

<400> SEQUENCE: 30

Ser Tyr Ser Met Glu His Phe Arg Trp Gly Lys Pro Val
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: misc_feature
<222> LOCATION: (1)..(1)
<223> OTHER INFORMATION: N-term acetylated
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 31

Ser Tyr Ser Leu Glu His Phe Arg Trp Gly Lys Pro Val
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (7)..(7)
<223> OTHER INFORMATION: D-Phe

<400> SEQUENCE: 32

Ser Tyr Ser Met Glu His Phe Arg Trp Gly Lys Pro Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (7)..(7)
<223> OTHER INFORMATION: D-Phe

<400> SEQUENCE: 33

Ser Tyr Ser Met Glu His Phe Arg Trp Gly Lys Pro Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ser
<220> FEATURE:
<221> NAME/KEY: MOD_RES
<222> LOCATION: (7)..(7)
<223> OTHER INFORMATION: D-Phe
```

```
<400> SEQUENCE: 34

Ser Tyr Ser Met Glu His Phe Arg Trp Gly Lys Pro Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Met
<220> FEATURE:
<221> NAME/KEY: MOD_RES
<222> LOCATION: (7)..(7)
<223> OTHER INFORMATION: D-Phe

<400> SEQUENCE: 35

Ser Tyr Ser Met Glu His Phe Arg Trp Gly Lys Pro Val
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (7)..(7)
<223> OTHER INFORMATION: D-Phe

<400> SEQUENCE: 36

Ser Tyr Ser Met Glu His Phe Arg Trp Gly Lys Pro Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Phe

<400> SEQUENCE: 37

Ser Tyr Ser Met Glu His Phe Arg Trp Gly Lys Pro Val
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: D-Arg

<400> SEQUENCE: 38

Ser Tyr Ser Met Glu His Phe Arg Trp Gly Lys Pro Val
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (9)..(9)
<223> OTHER INFORMATION: D-Trp

<400> SEQUENCE: 39

Ser Tyr Ser Met Glu His Phe Arg Trp Gly Lys Pro Val
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (11)..(11)
<223> OTHER INFORMATION: D-Lys

<400> SEQUENCE: 40

Ser Tyr Ser Met Glu His Phe Arg Trp Gly Lys Pro Val
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (12)..(12)
<223> OTHER INFORMATION: D-Pro

<400> SEQUENCE: 41

Ser Tyr Ser Met Glu His Phe Arg Trp Gly Lys Pro Val
1               5                   10
```

```
<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: D-Val

<400> SEQUENCE: 42

Ser Tyr Ser Met Glu His Phe Arg Trp Gly Lys Pro Val
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ser
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 43

Ser Tyr Ser Leu Glu His Phe Arg Trp Gly Lys Pro Val
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 44

Ser Tyr Ser Leu Glu His Phe Arg Trp Gly Lys Pro Val
1               5                   10

<210> SEQ ID NO 45
<211> LENGTH: 13
<212> TYPE: PRT
```

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: D-Ser
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe

<400> SEQUENCE: 45

Ser Tyr Ser Leu Glu His Phe Arg Trp Gly Lys Pro Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: D-Glu
<220> FEATURE:
<221> NAME/KEY: MOD_RES
<222> LOCATION: (7)..(7)
<223> OTHER INFORMATION: D-Phe

<400> SEQUENCE: 46

Ser Tyr Ser Leu Glu His Phe Arg Trp Gly Lys Pro Val
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: D-His
<220> FEATURE:
<221> NAME/KEY: MOD_RES
<222> LOCATION: (7)..(7)
<223> OTHER INFORMATION: D-Phe

<400> SEQUENCE: 47

Ser Tyr Ser Leu Glu His Phe Arg Trp Gly Lys Pro Val
1               5                   10

<210> SEQ ID NO 48
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (8)..(8)
<223> OTHER INFORMATION: D-Arg

<400> SEQUENCE: 48

Ser Tyr Ser Leu Glu His Phe Arg Trp Gly Lys Pro Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (9)..(9)
<223> OTHER INFORMATION: Trp

<400> SEQUENCE: 49

Ser Tyr Ser Leu Glu His Phe Arg Trp Gly Lys Pro Val
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (11)..(11)
<223> OTHER INFORMATION: D-Lys

<400> SEQUENCE: 50

Ser Tyr Ser Leu Glu His Phe Arg Trp Gly Lys Pro Val
1               5                   10

<210> SEQ ID NO 51
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (12)..(12)
<223> OTHER INFORMATION: D-Pro

<400> SEQUENCE: 51

Ser Tyr Ser Leu Glu His Phe Arg Trp Gly Lys Pro Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: D-Val

<400> SEQUENCE: 52

Ser Tyr Ser Leu Glu His Phe Arg Trp Gly Lys Pro Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(10)
<223> OTHER INFORMATION: Cyclic

<400> SEQUENCE: 53

Ser Tyr Ser Cys Glu His Phe Arg Trp Cys Lys Pro Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(10)
<223> OTHER INFORMATION: Cyclic
<220> FEATURE:
<221> NAME/KEY: MOD_RES
<222> LOCATION: (7)..(7)
```

```
<223> OTHER INFORMATION: D-Phe

<400> SEQUENCE: 54

Ser Tyr Ser Cys Glu His Phe Arg Trp Cys Lys Pro Val
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(11)
<223> OTHER INFORMATION: Cyclic

<400> SEQUENCE: 55

Ser Tyr Ser Cys Glu His Phe Arg Trp Gly Cys Pro Val
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(10)
<223> OTHER INFORMATION: Cyclic

<400> SEQUENCE: 56

Ser Tyr Ser Met Cys His Phe Arg Trp Cys Lys Pro Val
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(11)
<223> OTHER INFORMATION: Cyclic

<400> SEQUENCE: 57

Ser Tyr Ser Met Cys His Phe Arg Trp Gly Cys Pro Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: Cyclic

<400> SEQUENCE: 58

Cys Glu His Phe Arg Trp Cys Lys Pro Val
1               5                   10
```

```
<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: Cyclic

<400> SEQUENCE: 59

Cys Glu His Phe Arg Trp Cys Lys Pro
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 60

Leu Glu His Phe Arg Trp Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 61

Leu Glu His Phe Arg Trp Gly Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe

<400> SEQUENCE: 62

Glu His Phe Arg Trp Gly Lys
1               5
```

```
<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Tyr

<400> SEQUENCE: 63

Leu Glu His Tyr Arg Trp Gly Lys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (pNO2)D-Phe

<400> SEQUENCE: 64

Met Glu His Phe Arg Trp Gly Lys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe

<400> SEQUENCE: 65

Tyr Glu His Phe Arg Trp Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Phe

<400> SEQUENCE: 66

Tyr Glu His Phe Arg Trp Gly Lys
1               5

<210> SEQ ID NO 67
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle

<400> SEQUENCE: 67

Leu Glu His Phe Arg Trp Gly Lys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (pNO2)D-Phe

<400> SEQUENCE: 68

Leu Glu His Phe Arg Trp Gly Lys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-His

<400> SEQUENCE: 69

Leu Glu His Phe Arg Trp Gly Lys
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (3)..(3)
<223> OTHER INFORMATION: D-His
<220> FEATURE:
<221> NAME/KEY: MOD_RES
<222> LOCATION: (4)..(4)
```

```
<223> OTHER INFORMATION: D-Phe

<400> SEQUENCE: 70

Leu Glu His Phe Arg Trp Gly Lys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (5)..(5)
<223> OTHER INFORMATION: D-Arg

<400> SEQUENCE: 71

Leu Glu His Phe Arg Trp Gly Lys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: D-Trp

<400> SEQUENCE: 72

Leu Glu His Phe Arg Trp Gly Lys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 73

Leu Glu His Phe Arg Trp Gly Lys
1               5

<210> SEQ ID NO 74
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe

<400> SEQUENCE: 74

Leu Glu His Phe Arg Trp
1               5
```